(12) United States Patent
Kerver et al.

(10) Patent No.: US 7,089,049 B2
(45) Date of Patent: Aug. 8, 2006

(54) REMOVING POLARIZATION ARTIFACTS FROM ELECTRICAL ACTIVITY SIGNALS TO DETECT CARDIAC EVOKED RESPONSE

(75) Inventors: Harry Bernardus Antonius Kerver, Duiven (NL); Peter Oosterhoff, Zutphen (NL)

(73) Assignee: Medtronic, Inc., Minneapolis, MN (US)

( * ) Notice: Subject to any disclaimer, the term of this patent is extended or adjusted under 35 U.S.C. 154(b) by 548 days.

(21) Appl. No.: 10/424,928

(22) Filed: Apr. 25, 2003

(65) Prior Publication Data

US 2004/0215274 A1    Oct. 28, 2004

(51) Int. Cl.
*A61B 5/04*    (2006.01)
(52) U.S. Cl. ............................ 600/515; 607/14; 607/25
(58) Field of Classification Search ................. 607/14, 607/25; 600/515
See application file for complete search history.

(56) References Cited

U.S. PATENT DOCUMENTS

| 4,328,807 | A |   | 5/1982  | Jirak et al. |
|-----------|---|---|---------|--------------|
| 5,088,490 | A |   | 2/1992  | Pagliolo et al. |
| 5,511,554 | A | * | 4/1996  | Helfenbein et al. ......... 600/519 |
| 5,558,097 | A |   | 9/1996  | Jacobson et al. ........... 128/705 |
| 5,607,457 | A |   | 3/1997  | Schuller |
| 5,690,683 | A |   | 11/1997 | Haefner et al. ................. 607/4 |
| 6,064,906 | A | * | 5/2000  | Langberg et al. ........... 600/518 |
| 6,163,724 | A |   | 12/2000 | Hemming et al. |
| 6,192,275 | B1 |  | 2/2001  | Zhu et al. |
| 6,408,210 | B1 |  | 6/2002  | Bornzin et al. |
| 6,501,989 | B1 |  | 12/2002 | Uhrenius et al. |
| 6,925,331 | B1 | * | 8/2005 | Samuelson et al. ........... 607/32 |
| 2002/0188773 | A1 | | 12/2002 | Augustijn et al. |
| 2002/0193668 | A1 | | 12/2002 | Muhneke et al. |

FOREIGN PATENT DOCUMENTS

EP    0 748 637 A2    5/1996

OTHER PUBLICATIONS

Morrison et al., "Ventricular Evoked Response Measurements from Pacing Electrodes," Engineering in Medicine and Biology Society, 1995, IEEE 17th Annual Conference, pp. 331-332, vol. 1, 1997.

* cited by examiner

*Primary Examiner*—Robert E. Pezzuto
*Assistant Examiner*—Tammie K. Heller
(74) *Attorney, Agent, or Firm*—Daniel G. Chapik; Girma Wolde-Michael

(57) ABSTRACT

A medical device is directed to techniques for removing polarization artifacts from electrical activity signals in order to detect presence of an evoked response. More specifically, a medical device receives a signal that represents electrical activity within a heart of a patient following delivery of a stimulation pulse to the heart and reconfigures a filter state of a filter from an initial filter state to remove the polarization artifact from the electrical activity signal in order to determine whether a cardiac event, such as an evoked response, has occurred. The medical device may, for example, when the filter of the medical device is a digital filter, recalculate the values of digital filter components using the present input value of the electrical activity signal as a direct current (DC) input value of the digital filter.

34 Claims, 7 Drawing Sheets

REMOVING POLARIZATION ARTIFACTS FROM ELECTRICAL ACTIVITY SIGNALS TO DETECT CARDIAC EVOKED RESPONSE

FIELD OF THE INVENTION

The invention relates to cardiac evoked response detection and, more particularly, detection of evoked response in the presence of a polarization artifact following delivery of a stimulation pulse.

BACKGROUND OF THE INVENTION

Implantable medical devices, such as pacemakers, determine whether capture has occurred in response to a stimulation pulse in order to determine the effectiveness of the pacing therapy administered to the patient. The term "capture" generally refers to a cardiac depolarization and contraction of the heart in response to a stimulation pulse applied by the implantable medical device.

A common technique used to determine whether capture has been effectuated is to monitor the cardiac activity of a patient and to search for presence of an evoked response following a stimulation pulse. The evoked response is an electrical event that occurs in response to the application of the stimulation pulse to the heart. The cardiac activity of the patient is monitored by the medical device by tracking stimulation pulses delivered to the heart and examining, via one or more electrodes on leads deployed within the heart, electrical activity signals that occur concurrently with depolarization or contraction of the heart.

The evoked response is often difficult to detect due to a polarization artifact present on the sensing electrode employed to sense the electrical activity of the heart. This problem is especially prevalent in pacing systems that use the same lead to deliver the stimulation pulse and sense electrical activity of the heart after delivery of the stimulation pulse. Polarization of the pacing electrode is caused by accumulation of charge on an interface between the electrode and the cardiac tissue of the heart during delivery of a stimulation pulse.

The presence of the polarization artifact on the electrode can lead to errors in evoked response detection. For example, the generated polarization artifact may result in the pacemaker identifying a false evoked response, which in turn leads to missed heartbeats. Further, the polarization signal can cause the pacemaker to fail to detect an evoked response that is in fact present.

BRIEF SUMMARY OF THE INVENTION

In general, the invention is directed to techniques for reducing the effects of polarization artifacts in electrical activity signals in order to detect presence of an evoked response. The polarization artifacts result from the accumulation of charge on an interface between an electrode and cardiac tissue of a heart, i.e., the tissue-electrode interface, during delivery of a stimulation pulse to the heart. The invention processes sensed electrical signals via a filter. The filter, in effect, removes polarization artifacts from sensed electrical activity signals by reconfiguring a filter state of a filter from an initial filter state in order to determine existence of an evoked response following the stimulation pulse.

More specifically, a medical device receives a signal that represents electrical activity within the heart following delivery of a stimulation pulse to the heart and reconfigures a filter state of a filter from an initial filter state to remove a polarization artifact from the electrical activity signal in order to determine whether a cardiac event, such as an evoked response has occurred. The medical device may, for example, reconfigure the filter state after the filter output stabilizes, e.g., after an upward stroke of a filter step response, or at a predetermined time interval after delivery of the stimulation pulse.

The filter of the medical device may be a digital filter. In this case, the medical device recalculates digital filter components of the digital filter to remove the polarization artifact. Specifically, the medical device measures a present input value of the electrical activity signal and recalculates the values of the digital filter components using the present input value of the electrical activity signal as a direct current (DC) input value of the digital filter. In this manner, the output of the reconfigured digital filter has the filter step response caused by the polarization artifact removed and the medical device can more accurately determine presence of an evoked response.

Alternatively, the filter of the medical device may comprise an analog filter. For example, the analog filter of the medical device may include a first order high pass analog filter that includes a capacitor connected in series to a resistor and a switch, which are connected in parallel to one another. In accordance with the invention, the medical device closes the switch of the analog filter to load the capacitor with a present input value of the electrical activity signal and opens the switch to realize a reconfigured filter state of the analog filter. For example, the medical device may close the switch of the analog filter for approximately 1 millisecond to load the capacitor, in effect resetting the filter response following a decay in the polarization effects. Loading the capacitor with the present input value of the electrical activity signal has the same effect as calculating the filter components of the digital filter using the present input value of the electrical activity signal as a DC input value, e.g., it provides the analog filter with a DC offset value to remove the filter step response.

In one embodiment, the invention provides a method comprising receiving a signal that represents electrical activity within a heart following delivery of a stimulation pulse to the heart, reconfiguring a filter state of a filter from an initial filter state to remove an artifact from the electrical activity signal, and determining presence of a cardiac event based on the filtered electrical activity signal.

In another embodiment, the invention provides a medical device comprising at least one electrode to receive a signal that represents electrical activity within a heart following delivery of a stimulation pulse to the heart, a filter to filter the received electrical activity signal, a filter controller to reconfigure a filter state of the filter from an initial filter state to remove an artifact from the electrical activity signal, and a processor to determine presence of a cardiac event based on the filtered electrical activity signal.

In a further embodiment, the invention provides a computer-readable medium comprising instructions that cause a processor to receive a signal that represents electrical activity within a heart following delivery of a stimulation pulse to the heart, reconfigure a filter state of a filter from an initial filter state to remove an artifact from the electrical activity signal, and determine presence of a cardiac event based on the filtered electrical activity signal.

In another embodiment, the invention provides a medical device comprising means for receiving a signal that represents electrical activity within a heart following delivery of a stimulation pulse to the heart, means for reconfiguring a filter state of a filter from an initial filter state to remove an artifact from the electrical activity signal, and means for determining presence of a cardiac event based on the filtered electrical activity signal.

DETAILED DESCRIPTION OF THE INVENTION

In general, the invention is directed to techniques for removing post pace artifacts, such as polarization artifacts, from sensed cardiac electrical activity signals in order to more accurately detect capture following delivery of a stimulation pulse. The polarization artifacts result from the accumulation of charge on an electrode-tissue interface during delivery of a stimulation pulse. The invention removes polarization artifacts from sensed cardiac electrical activity signals by reconfiguring a filter state of a filter from an initial filter state in order to determine whether an evoked response occurs following a stimulation pulse. The evoked response is an electrical event that occurs in response to the application of the stimulation pulse to the heart, which indicates whether capture has been effectuated.

Figure 1:
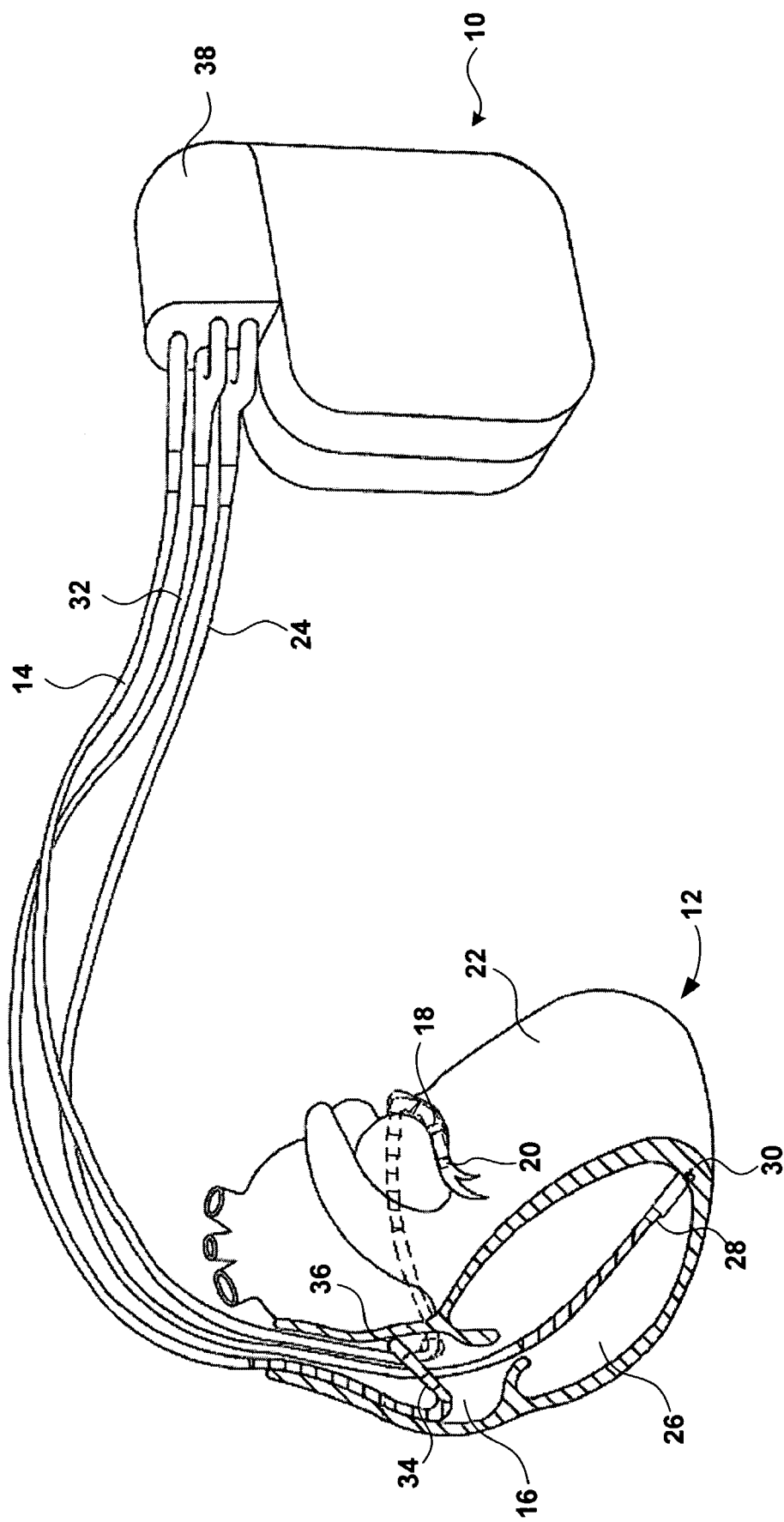
FIG. 1 is a conceptual diagram illustrating an exemplary implanted medical device (IMD) shown in conjunction with a heart of a patient.

FIG. 1 is conceptual diagram illustrating an exemplary implanted medical device (IMD) 10 shown in conjunction with a heart 12 of a patient. As will be described below, IMD 10 reconfigures a filter state of a filter from an initial filter state to remove a polarization artifact from a sensed electrical activity signal in order to determine presence of a cardiac event, such as an evoked response. Although a three-chamber IMD 10 and lead system is illustrated in FIG. 1 for purposes of illustration, methodologies implemented according to the present invention may be adapted for use with single chamber, dual chamber, or multi-chamber ICD or pacemaker systems, or cardiac monitoring devices. In addition, IMD 10 may include cardioversion and defibrillation functionality in addition to pacing functionality. For instance, IMD 10 can be a pacemaker-cardioverter-defibrillator (PCD). Although the invention can also find application in numerous other types of IMDs or external medical devices, the specific structure of IMD 10 is described herein for purposes of example.

In the example of FIG. 1, IMD 10 includes a left ventricular (LV) coronary sinus lead 14, which is passed through the superior vena cava into right atrium 16 of heart 12, into the coronary sinus and then inferiorly in the great vein and cardiac veins extending from the coronary sinus to extend a distal ring electrode 18 and tip electrode 20 alongside a left ventricle 22 of heart 12. A distal end of LV coronary sinus lead 14 positions the ring electrode 18 and tip electrode 20 with respect to the adjacent wall of left ventricle 22.

IMD 10 further includes a right ventricular (RV) lead 24 that is passed through the superior vena cava that leads into right atrium 16 and feeds into a right ventricle 26 of heart 12. RV lead 24 includes a distal ring electrode 28 and tip electrode 30 that are fixed in place in the apex or in the interventricular septum.

IMD also includes a right atrial (RA) lead 32 that is positioned within right atrium 16, with a distal end of RA lead 32 positioning a ring electrode 34 and a tip electrode 36 with respect to the adjacent wall of the right atrium 16 or positioned within the atrial appendage. The electrodes of the different leads can be used for pacing and sensing as well as for cardioversion or defibrillation. LV coronary sinus lead 14, RV lead 24 and RA lead 32 are inserted into a connector block 38 associated with IMD 10.

IMD 10 senses cardiac activity, i.e., electrical activity signals, via one or more of electrodes 18, 20, 28, 30, 34, and 36 following delivery of a stimulation pulse to heart 12. In accordance with the invention, IMD 10 reconfigures a filter state of a filter from an initial filter state to remove the polarization artifact from the electrical activity signal in order to determine presence of a cardiac event. IMD 10 may, for example, reconfigure the filter as soon as a step portion of the polarization artifact passes following reconnection of the filter after delivery of the stimulation pulse. The cardiac event of interest can include presence of an evoked response, presence of a T-wave, or other cardiac events that are sensed following application of a therapy to heart 12.

Although described in terms of removing a polarization artifact from a sensed electrical activity signal, the techniques of the invention may be used more generally to remove filter responses due to large input step signals (i.e., artifact) to allow detection or measurement of smaller signals that may normally be unobservable due to the immediately preceding large input step signal. In this manner, the techniques increase the visibility of the filter's response to the smaller input signals. One example is the situation where a filter at a certain moment is connected to an input signal that has a large DC offset signal (e.g., the offset or operating point voltage of an amplifier in the signal path or a DC voltage that is present between electrodes of different materials). By applying the techniques of the invention immediately following or shortly after the moment of connection of the amplifier to the large DC offset signal, the filter response to the input signal step is removed, allowing processing of the input signals immediately after the moment of connection, without having to wait for the filter response to the input signal step to disappear.

Figure 2:
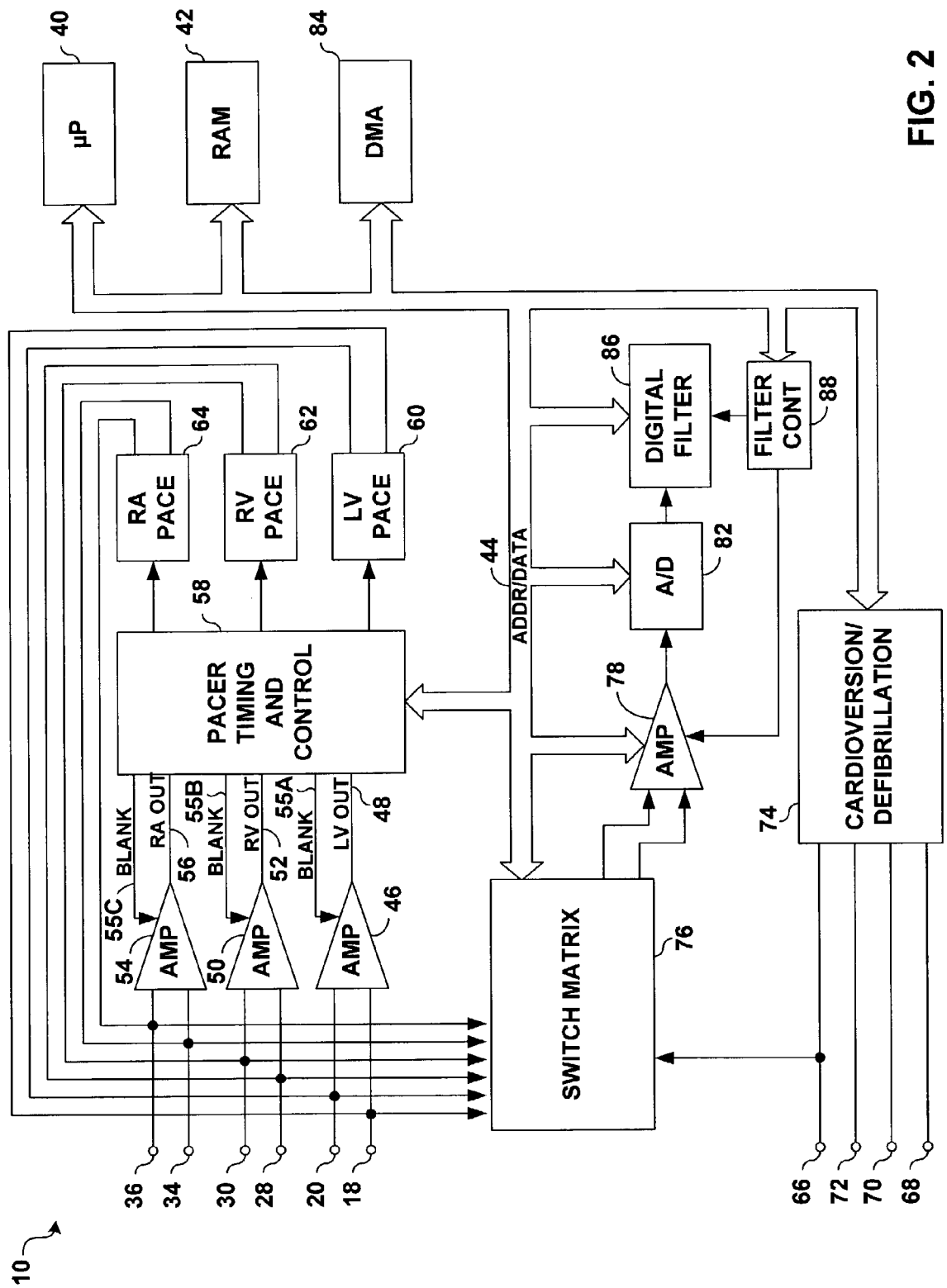
FIG. 2 is a functional block diagram of the IMD of FIG. 1.

FIG. 2 is a functional block diagram of an embodiment of IMD 10, such as that shown in FIG. 1, in which IMD 10 comprises a pacemaker that includes pacing, defibrillation, and cardioversion functionality. The diagram of FIG. 2 should be taken as exemplary of the type of device in which various embodiments of the present invention may be embodied, and not as limiting, as the invention could be practiced in a wide variety of device implementations, including devices that provide pacing therapies but do not provide cardioversion and/or defibrillation therapy.

In the example of FIG. 2, IMD 10 includes a microprocessor 40 that executes program instructions stored in memory, such as a read only memory (ROM) (not shown), an electrically erasable programmable read-only memory (EEPROM) (not shown), and/or a random access memory (RAM) 42, which control microprocessor 40 to perform the functions ascribed to microprocessor 40 herein. Microprocessor 40 is coupled to various other components of IMD 10 via an address/data bus 44 to communicate with and/or control those components.

As shown in FIG. 2, IMD 10 includes an electrode system for receiving electrical activity signals from heart 12 as well as providing therapy, e.g., stimulation pulses, to heart 12. Electrodes 18 and 20 are coupled to amplifier 46. Amplifier 46 may be an amplifier with an adjustable sensing threshold. As illustrated in FIG. 1, electrodes 18 and 20 are positioned proximate to a distal end of LV coronary sinus lead 14. A signal is generated on LV out line 48 whenever the signal sensed between electrodes 18 and 20 exceeds the present sensing threshold.

Electrodes 28 and 30 are coupled to amplifier 50, which also can take the form of an amplifier with an adjustable sensing threshold. For instance, electrodes 28 and 30 are positioned proximate to a distal end of RV lead 24 as illustrated in FIG. 1. A signal is generated on RV out line 52 whenever the signal sensed between electrodes 28 and 30 exceeds the present sensing threshold.

Electrodes 34 and 36 are coupled to amplifier 54, which can take the form of an amplifier with an adjustable sensing threshold. In the example of FIG. 1, electrodes 34 and 36 are positioned proximate to distal end of RA lead 32. A signal is generated on RA out line 56 whenever the signal between electrodes 34 and 36 exceeds the present sensing threshold.

Amplifiers 46, 50 and 54 receive timing information from pacer timing and control circuitry 58. Specifically, amplifiers 46, 50 and 54 receive blanking period input 55A–55C, e.g., BLANK, which indicates an amount of time the electrodes are "turned off" in order to prevent saturation due to an applied stimulation pulse, e.g., a pacing pulse or defibrillation shock.

IMD 10 further includes a can electrode 66, which is formed by an uninsulated portion of a housing of IMD 10 or by the whole housing of IMD 10. IMD 10 further includes elongated coil electrodes 68, 70, and 72. Coil electrodes 68, 70, and 72 are positioned along one or more of leads 14, 24, and 32. Can electrode 66 and coil electrodes 68, 70 and 72 are coupled to cardioversion/defibrillation circuit 74. Cardioversion/defibrillation circuit 74 includes energy storage circuits such as capacitors, switches for coupling the storage circuits to electrodes 66, 68, 70 and 72, and logic for controlling the coupling of the storage circuits to the electrodes to create pulses with desired polarities and shapes.

Switch matrix 76 is used to select which of the available electrodes are coupled to filter amplifier 78 for use in digital signal analysis. Selection of electrodes is controlled by microprocessor 40 via data/address bus 44, and the selections are varied as desired. Electrical activity signals from the electrodes selected for coupling to filter amplifier 78 are converted to multi-bit digital signals by A/D converter 82, for processing by a digital filter 86 or processor 40. Both the data from A/D converter 82 and the data filtered by digital filter 86 are available for storage in RAM 42 under control of direct memory access (DMA) circuit 84.

In accordance with the invention, IMD 10 removes post pace artifacts, such as polarization artifacts, from the electrical activity signals sensed by all or a portion of electrodes 18, 20, 28, 30, 34, and 36. Particularly, IMD 10 and, more particularly, a filter controller 88 reconfigures a filter state of a filter, e.g., digital filter 86, from an initial filter state to remove the polarization artifact from the electrical activity signal.

Filter controller 88 may be programmed to reconfigure the filter state of the filter as soon as a step-up portion of a filter step response due to the polarization artifact has passed, i.e., the filter has stabilized. In one embodiment, filter controller 88 recalculates values of digital filter components of digital filter 86 to remove polarization artifacts from sensed electrical activity signals. Specifically, filter controller 88 recalculates the digital filter component values using the present input of the electrical activity signal as a constant DC input value of the filter. For example, filter controller 88 may recalculate one or more gain coefficients or time constants associated with digital filter 86. Digital filter 86 may be implemented within a digital signal processor (DSP). In some embodiments, microprocessor 40 may take the form of a DSP, or microprocessor 40 can perform the digital filtering.

In another embodiment, filter controller 88 reconfigures an analog filter, such as the analog filter component of filter amplifier 78 or a separate analog filter within IMD 10, to remove polarization artifacts from electrical activity signals. Particularly, using a first order analog filter as an example, filter controller 88 closes a switch of the analog filter to load a capacitor of the filter with a present input value of the sensed electrical activity signal and then opens the switch to realize a reconfigured filter state.

The remainder of the circuitry in the example of FIG. 2 is dedicated to delivery of cardiac pacing, cardioversion and defibrillation therapies, which may be responsive to data obtained by IMD 10 via leads 14, 24, 32. Pacer timing/control circuitry 58 includes programmable digital counters, which control the basic time intervals associated with modes of pacing. Pacer timing/control circuitry 58 also controls escape intervals associated with pacing. Pacer timing/control circuitry 58 also determines the amplitude of the cardiac pacing pulses under control of microprocessor 40.

During pacing, escape interval counters within pacer timing/control circuitry 58 are reset upon sensing of R-waves and P-waves as indicated by signals on lines 48, 52 and 56. In accordance with the selected mode of pacing, pacer timing/control circuitry 58 triggers generation of pacing pulses by pacer output circuitry 60, 62 and 64 which are coupled to electrodes 18, 20, 28, 30, 34 and 36.

The embodiment shown in FIG. 2 is merely exemplary. For example, the embodiment shown in FIG. 2 may be modified to include additional features, or may be adapted to other embodiments. In particular, the embodiment in FIG. 2 may be modified for an implanted medical device having electrodes mounted on any number of leads not shown in FIG. 1, or may not include one or more of the leads shown in FIG. 1. The embodiment shown in FIG. 2 can, for example, be modified to detect activity in or near the left atrium of the patient.

The invention can find wide application to any form of implantable medical device or possibly external medical devices that analyze electrical activity signals with post pace artifacts, such as polarization artifacts. Although IMD 10 is described herein as having separate components for filtering the signals and controlling the filters, microprocessor 40 may perform both the functions ascribed to it herein and filter control functions ascribed to filter controller 88 and filtering functions ascribed to digital filter 86. Moreover, although described herein in the context of microprocessor based IMD 10, in some embodiments the invention is embodied in various IMDs that include one or more processors, which may be microprocessors, DSPs, ASICS, FPGAs, or other digital logic circuits.

Figure 3:
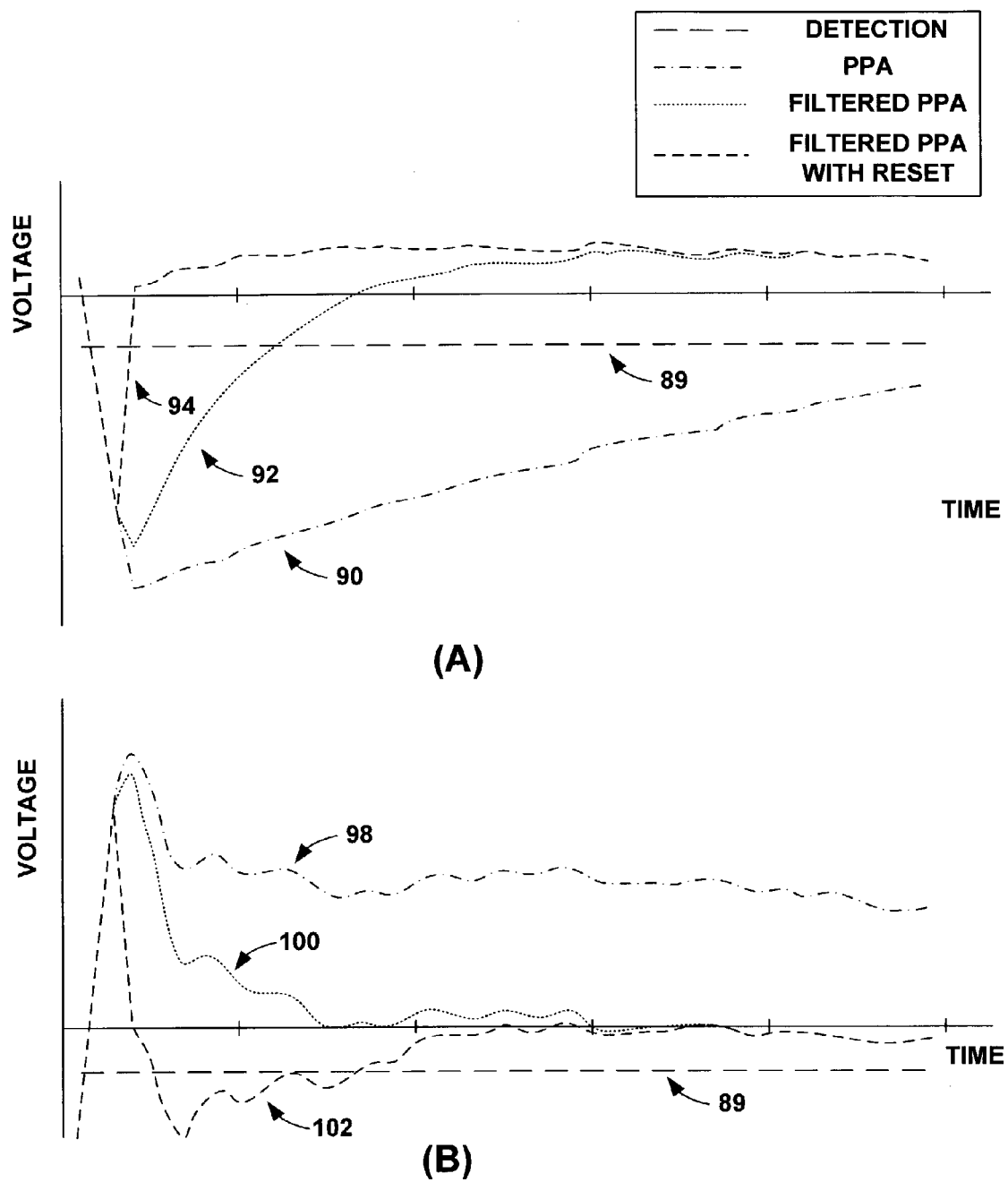
FIG. 3 is a graph that illustrates electrical activity signals with polarization artifacts filtered in accordance with the invention.

FIG. 3 is a graph that illustrates exemplary electrical activity signals with polarization artifacts. More specifically, FIG. 3(A) illustrates an electrical activity signal that includes a negative polarization artifact without the presence of an evoked response, e.g., after delivery of a stimulation pulse that does not capture heart 12 of a patient. FIG. 3(B) illustrates a sensed electrical activity signal that includes a positive polarization artifact as well as an evoked response signal, e.g., after delivery of a stimulation pulse that does capture heart 12 of a patient. In the graphs illustrated in FIGS. 3(A) and 3(B), IMD 10 uses a negative detection threshold level 89 to detect evoked response of heart 12. In other words, IMD 10 detects an evoked response when the electrical activity signal falls below negative detection threshold level 89.

Before IMD 10 delivers a stimulation pulse to heart 12, IMD 10 disconnects, i.e., turns off, amplifiers that couple to stimulation and sensing electrodes coupled to heart 12 in order to prevent saturation of the amplifiers due to the delivered stimulation pulse. IMD 10 may turn off the amplifiers by sending the amplifiers blanking period input before delivering stimulation pulses to heart 12, as briefly described above with respect to FIG. 2. Upon reconnection of the amplifiers to the electrodes, an electrical activity signal is obtained with a polarization artifact, either positive or negative depending on the type of stimulation pulse applied to heart 12.

As illustrated by the graph in FIG. 3(A), IMD 10 falsely detects an evoked response due to a negative polarization artifact 90. More specifically, negative polarization artifact 90, caused by the accumulation of charge on an electrode-tissue interface during delivery of a stimulation pulse, drives the electrical activity signal below detection threshold level 89, causing IMD 10 to falsely identify an evoked response. Negative polarization artifact 90 comprises a sudden negative input change, i.e., a negative step, followed by a slow decay towards an electrode potential seen in the absence of any stimulus. In this manner, the negative polarization artifact signal can be viewed as a negative step-like signal. Negative polarization artifact signal 90 remains below the negative detection threshold for an extended period of time causing IMD 10 to detect a false evoked response.

The slow decay of negative polarization artifact 90 can be removed by filtering the negative polarization artifact signal 90 with a high pass digital filter as illustrated by a filtered polarization artifact signal 92. In alternate embodiments, a high pass analog filter, such as a discrete analog filter component or a filter component of a filter amplifier, e.g., filter amplifier 78 (FIG. 2). However, the sudden start of negative polarization artifact signal 90, i.e., the negative step portion of negative polarization artifact signal 90, evokes a filter step response in the filter output.

The filter step response illustrated by filtered polarization artifact signal 92 includes a negative step similar to the negative step of negative polarization signal 90 and a decay portion that decays towards an electrode potential seen in the absence of any stimulus faster than the decay portion of negative polarization signal 90. Although the decay of filtered polarization artifact signal 92 is faster than negative polarization artifact signal 90, it still may cause IMD 10 to detect a false evoked response. For example, IMD 10 may perform evoked response detection before filtered polarization artifact signal 92 rises above negative threshold detection level 89, resulting in a false evoked response.

In accordance with the invention, IMD 10 removes negative polarization artifact signal 90, e.g., the upward stroke or step as well as the slow decay, from the electrical activity signal by reconfiguring a filter state of the filter from an initial filter state. The resulting electrical activity signal is illustrated by line 94. More specifically, IMD 10 reconfigures the filter state of the filter as soon as the step portion of the polarization artifact signal 90 has passed in order to remove the filter step response of the filter. In other words, IMD 10 reconfigures the filter state of the filter after the filter becomes stabilized. IMD 10 further removes the slow decay via filtering of the polarization artifact signal with a high pass filter. In this manner, the electrical activity signal filtered by the reconfigured filter rises above negative threshold detection level 89 to reduce the likelihood of false evoked response detection.

As described above, the filter may either be a digital filter or an analog filter. However, use of a digital filter advantageously allows IMD 10 to use more complex filters, e.g., higher order filters. In the case that the filter is a digital filter, IMD 10 recalculates values of digital filter components of the digital filter using an input value of the electrical activity signal at the time of reconfiguration of the digital filter as a DC input value for the digital filter. In the case in which the filter is an analog filter and, more particularly, a first order analog filter, IMD 10 closes a switch to load a capacitor with a current input value of the electrical activity signal and opens the switch to realize the reconfigured filter state. Loading the capacitor with the present input value of the electrical activity signal has the same effect as calculating the filter components of the digital filter using the present input value of the electrical activity signal as a DC input value.

FIG. 3(B) illustrates a sensed electrical activity signal 98 that includes a positive polarization artifact as well as an evoked response signal. As illustrated in FIG. 3(B), the step portion of the positive polarization artifact raises electrical activity signal 98 above negative detection threshold level 89. The evoked response lowers electrical activity signal 98 towards negative detection threshold level 89, but the positive polarization signal is much larger than the negative step of the evoked response. In this way, the positive polarization artifact can be seen as a positive DC offset value. Because the positive polarization signal is much larger than the negative step of the evoked response, the positive polarization artifact causes IMD 10 to inaccurately detect no evoked response, when, in fact, an evoked response is present.

As seen by line 100, which represents a filtered version of electrical activity filter with no reconfiguration of the filter state, filtering of the electrical activity signal with the positive polarization and the evoked response improves the sensed signal, but it still results in an undetected evoked response.

However, when IMD 10 reconfigures a filter state of a high pass filter from an initial filter state, the step portion of the positive polarization artifact is reduced enough to enable the evoked response to drive the electrical activity signal below negative threshold detection level 89 (illustrated by line 102). In this manner, reconfiguring the filter states of the input filters and filtering the electrical activity signals in accordance with the reconfigured filters results in correct evoked response detection.

Figure 4:
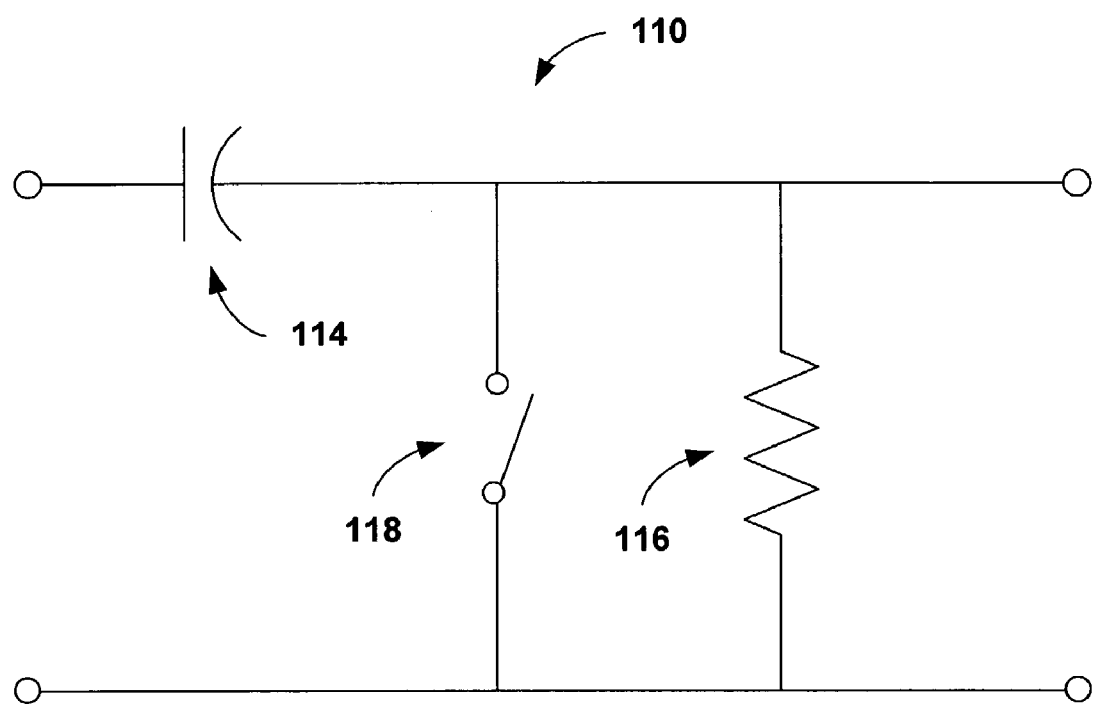
FIG. 4 is a circuit diagram illustrating an exemplary analog filter used to remove a polarization artifact from an electrical activity signal in accordance with the invention.

FIG. 4 is a circuit diagram illustrating an exemplary analog filter 110 used to remove a polarization artifact from an electrical activity signal in accordance with the invention. A filter controller, such as filter controller 88 of FIG. 2, reconfigures a filter state of analog filter 110 in order to remove the polarization artifact from the received electrical activity signal. Although the example of FIG. 4 is described in terms of a first order analog filter 110, the techniques of the invention may be applied to higher order analog filters.

In the example illustrated in FIG. 4, analog filter 110 is a first order high pass filter that includes a capacitor 114, resistor 116 and switch 18. More specifically, capacitor 110 of analog filter 110 is connected in series with a resistor 116 and a switch 118, which are connected in parallel with one another. In accordance with the invention, filter controller 88 closes switch 118 to load capacitor 114 with a present value of the electrical activity signal at the time at which switch 118 is closed.

Filter controller 88 may close switch 118 upon a peak amplitude of the electrical activity signal or after a defined time interval after reconnecting an amplifier to the electrodes. Filter controller 88, for example, closes switch 118 for approximately 1 millisecond to load capacitor 114 with the present value of the electrical activity signal. Upon opening switch 118, the output of analog filter 110 changes as a function of the input electrical activity signal. In this manner, the loaded capacitor 114 removes the sudden start associated with the step response due to the polarization signal while analog filter 110 removes the slow decay of the step response, as discussed in FIG. 3.

Figure 5:
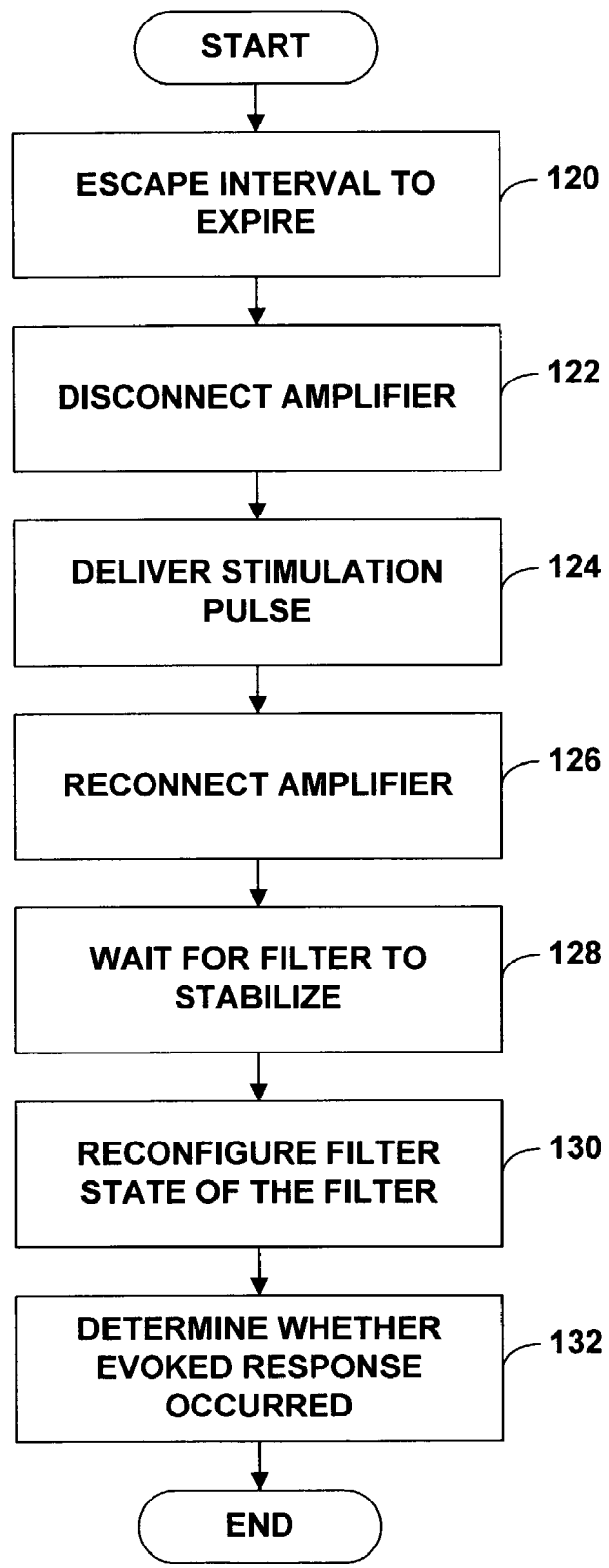
FIG. 5 is a flow diagram illustrating exemplary operation of an IMD stimulating and sensing a heart of a patient.

FIG. 5 is a flow diagram illustrating exemplary operation of IMD 10 stimulating and sensing heart 12. Initially, pacer timing/control circuitry 58 of IMD 10 waits for an escape interval to expire, indicating a need to deliver a stimulation pulse to heart 12 (120). During generation of the stimulation pulse, pacer timing/control circuitry 58 disconnects, i.e., turns off, an amplifier coupled to stimulation and sensing electrodes in order to prevent saturation of the amplifier due to the stimulation pulse (122). IMD 10 delivers the stimulation pulse to the respective chamber of heart 12 via electrodes coupled to heart 12 (124).

After delivery of the stimulation pulse to heart 12, IMD 10 reconnects the amplifier to the respective electrodes, e.g., ring and tip electrodes of a cardiac lead attached to heart 12 (126). As described above, the stimulation pulse delivered to heart 12 causes a polarization artifact as result of an accumulation of charge on an electrode-tissue interface, during delivery of the stimulation pulse. The sudden start of the polarization artifact, i.e., the upward stroke of the step portion of the polarization artifact, evokes a step response in a filter of IMD 10. The filter of IMD 10 may be a digital filter such as digital filter 86 of FIG. 2. The digital filter may be implemented in hardware or software and may be executed within microprocessor 40 or a digital signal processor (DSP). In some embodiments, however, the filter is an analog filter. For example, the analog filter may be a filter component of a filter amplifier, such as filter amplifier 78 of FIG. 4, or a discrete analog filter component.

In accordance with the invention, a filter controller 88 waits for the filter to stabilize (128) and reconfigures a filter state of the filter from an initial filter state to remove the polarization artifact from the sensed electrical activity signal (130). Filter controller 88 considers the filter to be stabilized, for example, when the upward stroke of the filter step response has passed. Filter controller 88 may, for example, determine the filter to be stabilized upon identifying a sign change in a slope of the electrical activity signal, i.e., a sign change in the first derivative of the electrical activity signal. Alternatively, in some embodiments, filter controller 88 may reconfigure the filter state of the filter a defined time interval after reconnecting the amplifier. Filter controller 88 may, for example, consider the filter to be stabilized based on timing information received from microprocessor 40, or timing information received from pacer timing and control circuit 58.

Reconfiguration of the filter state of the filter to remove the polarization artifact from the electrical activity signal may include, for example, filter controller 88 recalculating filter components of a digital filter using the present value of the electrical activity signal as a DC input value. For the case in which the filter is an analog filter, reconfiguration of the filter state of the filter to remove the polarization artifact from the electrical activity signal includes closing a switch of an analog filter to load a capacitor of the analog filter with the present value of the electrical activity signal. The digital filter implementation within IMD 10 allows IMD 10 to use more complex filters, e.g., higher order filters, than the analog filter implementation.

Microprocessor 40 of IMD 10 proceeds to determine whether an evoked response occurred by analyzing the filtered electrical activity signal (132). Microprocessor 40, for example, analyzes the filtered signal and determines whether the filtered signal, which no longer includes the polarization artifact, exceeds a defined detection level. When the filtered signal exceeds the detection level, an evoked response is detected, which indicates that the potential of the stimulation pulse is sufficient to evoke capture of heart 12. When the filtered signal does not exceed the detection level, an evoked response does not occur, indicating that the potential of the stimulation pulse is not sufficient to evoke capture. Alternatively, in some embodiments, IMD 10 performs detection of the evoked response using a threshold detection circuit (not shown) that determines whether the filtered signal, which no longer includes the polarization artifact, exceeds a defined detection level. The threshold detection circuit passes information to microprocessor 40 or pacer timing and control block 58 to identify whether the potential of the stimulation pulse was sufficient to evoke capture.

Figure 6:
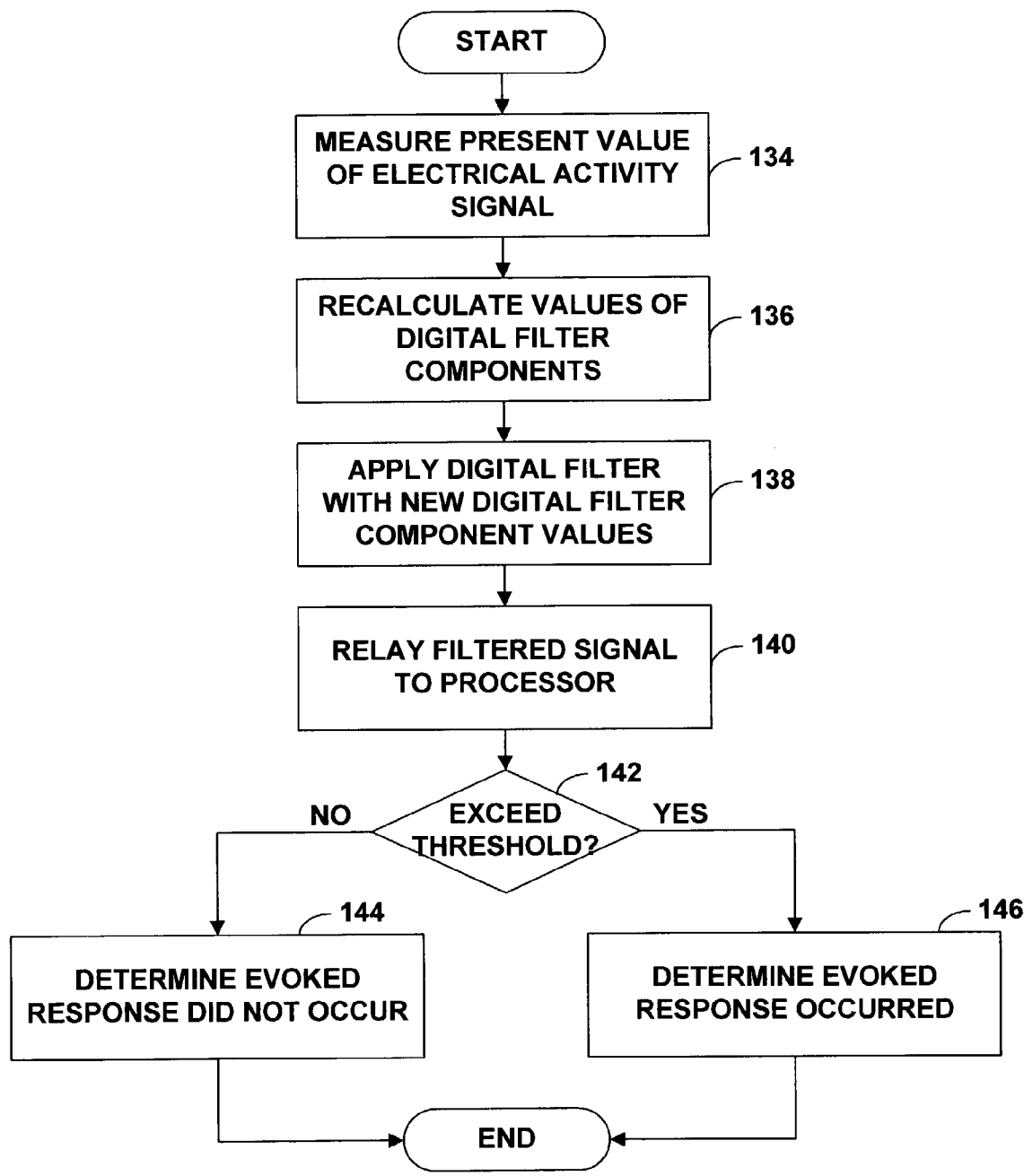
FIG. 6 is a block diagram illustrating exemplary operation of an IMD reconfiguring a digital filter to remove a polarization artifact to determine presence of an evoked response in accordance with the invention.

FIG. 6 is a block diagram illustrating exemplary operation of IMD 10 reconfiguring a digital filter to remove a polarization artifact to determine presence of an evoked response in accordance with the invention. Upon stabilization of the digital filter, filter controller 88 measures the present value of the electrical activity signal (134). Next, filter controller 88 recalculates the values for digital filter components using the present input value of the electrical activity signal, measured previously, as a DC input value of the digital filter (136). In this manner, the filter state of the filter is reconfigured in order to eliminate the step response caused by the polarization artifact.

Digital filter 86 applies the new digital filter component values to electrical activity signals received to filter the electrical activity signals (138). The output of the digital filter is relayed to microprocessor 40 (140) to determine whether the filtered electrical activity signal exceeds a defined detection level (142). When the electrical activity signal filtered in accordance with the invention does not exceed the detection level, microprocessor 40 determines that the stimulation pulse delivered to heart 12 did not evoke capture, i.e., there was no evoked response within the electrical activity signal (144). When the electrical activity signal filtered in accordance with the invention exceeds the detection level, microprocessor 40 determines that the stimulation pulse delivered to heart 12 evoked capture, i.e., there was an evoked response within the electrical activity signal (146).

The techniques described for reconfiguration of the digital filter to remove the polarization artifact from the electrical activity signal can be used with first order digital filters as well as higher order digital filters, i.e., digital filters with an order higher than one.

Figure 7:
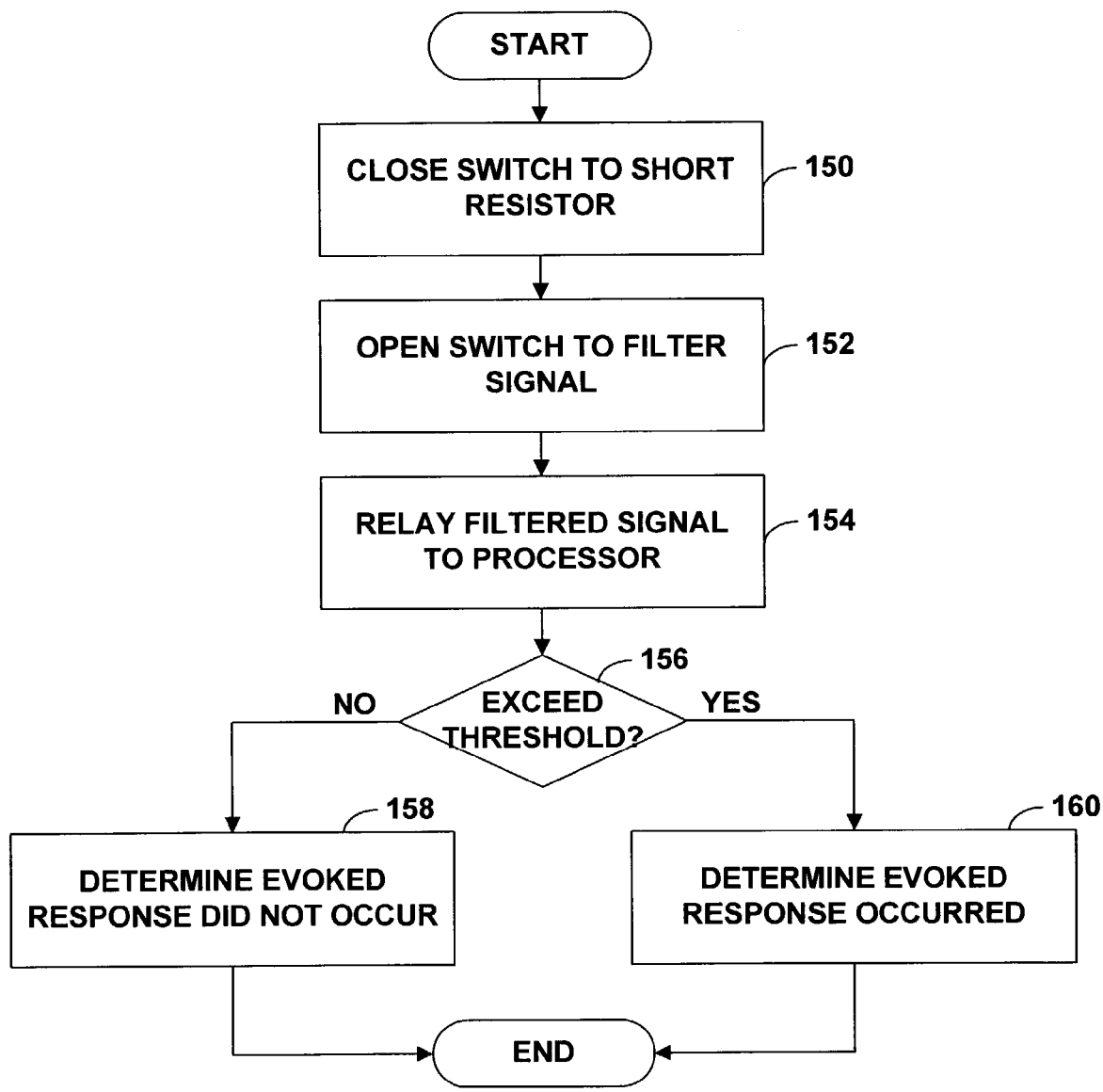
FIG. 7 is a flow diagram illustrating exemplary operation of an IMD reconfiguring an analog filter to remove a polarization artifact to determine presence of an evoked response in accordance with the invention.

FIG. 7 is a flow diagram illustrating exemplary operation of IMD 10 reconfiguring an analog filter 110 to remove a polarization artifact to determine presence of an evoked response in accordance with the invention. Upon stabilization of analog filter 110 output, i.e., after the upward stroke of the step response due to the polarization artifact, filter controller 88 closes switch 118 to load capacitor 114 with the present value of the electrical activity signal (150). Filter controller 88, for example, may close switch 118 for approximately 1 millisecond to load capacitor 114 with the present value of the electrical activity signal. Loading capacitor 114 with the present input value of the electrical activity signal has the same effect as calculating the filter components of the digital filter using the present input value of the electrical activity signal as a DC input value, e.g., provides the filter 110 with a DC offset value.

Filter controller 88 opens switch 118 to realize a reconfigured filter state (152). Upon opening switch 118, the output of analog filter 110 changes as a function of the input electrical activity signal. In this manner, the loaded capacitor 114 removes the sudden start associated with the step response due to the polarization signal while analog filter 110 removes the slow decay of the step response, as discussed in FIG. 3.

Analog filter 110 filters the electrical activity signal in accordance with the reconfigured filter state and relays the output to a microprocessor 40 to determine whether an evoke response occurs (154) by determining whether the filtered electrical activity signal exceeds a defined detection level (156). When the filtered electrical activity signal does not exceed the detection level, microprocessor 40 determines that the stimulation pulse delivered to heart 12 did not evoke capture, i.e., there was no evoked response within the electrical activity signal (158). When the filtered electrical activity signal exceeds the detection level, microprocessor 40 determines that the stimulation pulse delivered to heart 12 evoked capture, i.e., there was an evoked response within the electrical activity signal (160).

Various embodiments of the invention have been described. Although described in terms of polarization artifacts and evoked response detections, the techniques of the invention may be applied to remove any type of step-like post pace artifact from an electrical activity signal to detect and some sort of cardiac response. For example, instead of detecting evoked responses, the techniques of the invention may be use to detect T-waves. These and other embodiments are within the scope of the following claims.

What is claimed is:

1. A method comprising:
   receiving a signal that represents electrical activity within a heart following delivery of a stimulation pulse to the heart;
   reconfiguring a filter state of a filter from an initial filter state to remove an artifact from the electrical activity signal, wherein the filter comprises a digital filter and reconfigiuring the filter state of the filter comprises recalculating values of digital filter components of the digital filter by measuring a present input value of the electrical activity signal and recalculating the values of the digital filter components using the present input value of the electrical activity signal as a direct current (DC) input value of the digital filter; and
   determining presence of a cardiac event based on the filtered electrical activity signal.

2. The method of claim 1, wherein the artifact comprises a polarization artifact.

3. The method of claim 1, wherein reconfiguring the filter state of the filter comprises reconfiguring the filter state of the filter at a peak amplitude of the electrical activity signal.

4. The method of claim 1, wherein reconfiguring the filter state of the filter comprises reconfiguring the filter state of the filter at a defined time interval after turning on the filter.

5. The method of claim 1, wherein measuring the present input value of the electrical activity signal comprises measuring the present input value of the electrical activity signal upon stabilization of a filter output.

6. The method of claim 1, wherein the filter comprises an analog filter and reconfiguring the filter state of the filter state of the filter comprises closing a switch of the analog filter to load a capacitor with a present input value of the electrical activity signal.

7. The method of claim 6, further comprising opening the switch to output an electrical activity signal with the artifact removed.

8. The method of claim 6, wherein the analog filter comprises a first order analog filter.

9. The method of claim 1, wherein the filter comprises a high pass filter.

10. The method of claim 1, wherein determining whether a cardiac event occurs comprises determining whether the filtered electrical activity signal exceeds a detection level.

11. The method of claim 1, wherein determining presence of a cardiac event based on the filtered electrical activity signal comprises determining presence of an evoked response based on the filtered electrical activity signal.

12. The method of claim 1, wherein determining presence of a cardiac event based on the filtered electrical activity signal comprises determining presence of T-wave based on the filtered electrical activity signal.

13. A medical device comprising:
   at least one electrode to receive a signal that represents electrical activity within a heart following delivery of a stimulation pulse to the heart;
   a filter to filter the received electrical activity signal;
   a filter controller to reconfigure a filter state of the filter from an initial filter state to remove an artifact from the electrical activity signal, wherein the filter comprises a digital filter, and the filter controller recalculates values of digital filter components of the digital filter and the filter controller measures a present input value of the electrical activity signal and recalculates the values of the digital filter components using the present input value of the electrical activity signal as a direct current (DC) input value of the digital filter; and
   a processor to determine presence of a cardiac event based on the filtered electrical activity signal.

14. The device of claim 13, wherein the artifact comprises a polarization artifact.

15. The device of claim 13, wherein the filter controller reconfigures the filter state of the filter at a peak amplitude of the electrical activity signal.

16. The device of claim 13, wherein the filter controller reconfigures the filter state of the filter at a defined time interval after turning on the filter.

17. The device of claim 13, wherein the filter controller measures the present input value of the electrical activity signal upon stabilization of a filter output.

18. The device of claim 13, wherein an order of the digital filter is greater than or equal to one.

19. The device of claim 13, wherein the filter comprises an analog filter, and the filter controller closes a switch of the analog filter to load a capacitor with a present input value of the electrical activity signal.

20. The device of claim 19, wherein the filter controller opens the switch to output an electrical activity signal with the artifact removed.

21. The device of claim 19, wherein the analog filter comprises a first order analog filter.

22. The device of claim 13, wherein the filter comprises a high pass filter.

23. The device of claim 13, wherein the processor compares the filtered electrical activity signal to a defined detection level and determines presence of a cardiac event when the filtered signal exceeds the detection level.

24. The device of claim 13, wherein the cardiac event includes one of an evoked response of the heart or a T-wave contraction of the heart.

25. The device of claim 13, wherein the electrode delivers the stimulation pulse and receives the electrical activity signal.

26. The device of claim 13, wherein the medical device comprises an implanted medical device.

27. A computer-readable medium comprising instructions that cause a processor to:
　receive a signal that represents electrical activity within a heart following delivery of a stimulation pulse to the heart;
　reconfigure a filter state of a filter from an initial filter state to remove an artifact from the electrical activity signal, wherein instructions that cause a processor to reconfigure the filter state of the filter includes instructions that cause a processor to recalculate values of digital filter components of the digital filter wherein instructions that cause a processor to recalculate the values of the digital filter components includes instructions that cause a processor to measure a present input value of the electrical activity signal and recalculate the values of the digital filter components using the present input value of the electrical activity signal as a direct current (DC) input value of the digital filter; and
　determine presence of a cardiac event based on the filtered electrical activity signal.

28. The computer-readable medium of claim 27, wherein instructions that cause a processor to measure the present input value of the electrical activity signal comprises instructions that cause a processor to measure the present input value of the electrical activity signal upon stabilization of a filter output.

29. The computer-readable medium of claim 27, wherein instructions that cause a processor to determine whether a cardiac event occurs comprises instructions that cause a processor to determine whether the filtered electrical activity signal exceeds a detection level.

30. A medical device comprising:
　means for receiving a signal that represents electrical activity within a heart following delivery of a stimulation pulse to the heart;
　means for reconfiguring a filter state of a filter from an initial filter state to remove an artifact from the electrical activity signal; and
　means for determining presence of a cardiac event based on the filtered electrical activity signal, wherein the filter comprises a digital filter, and the wherein the means for reconfiguring recalculates values of digital filter components of the dgital filter and the means for reconfiguring measures a present input value of the electrical activity signal and recalculates the values of the digital filter components using the present input value of the electrical activity signal as a direct current (DC) input value of the digital fitter.

31. The device of claim 30, wherein the artifact comprises a polarization artifact.

32. The device of claim 30, wherein the means for reconfiguring reconfigures the filter state of the filter at a peak amplitude of the electrical activity signal.

33. The device of claim 30, wherein the means for reconfiguring reconfigures the filter state of the filter at a defined time interval after turning on the filter.

34. The device of claim 30, wherein the filter comprises an analog filter, and the means for reconfiguring closes a switch of the analog filter to load a capacitor with a present input value of the electrical activity signal and opens the switch to output an electrical activity signal with the artifact removed.

* * * * *